(12) United States Patent
Schoepgens et al.

(10) Patent No.: US 10,413,499 B2
(45) Date of Patent: Sep. 17, 2019

(54) OXIDATIVE HAIR TREATMENT WITH POST-TREATMENT FOR IMPROVING FASTNESS TO WASHING

(71) Applicant: Henkel AG & Co. KGaA, Duesseldorf (DE)

(72) Inventors: Juergen Schoepgens, Schwalmtal (DE); Burkhard Mueller, Dusseldorf (DE); Anja Reichert, Duesseldorf (DE); Daniela Kessler-Becker, Leverkusen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 56 days.

(21) Appl. No.: 15/846,216

(22) Filed: Dec. 19, 2017

(65) Prior Publication Data

US 2018/0168980 A1    Jun. 21, 2018

(30) Foreign Application Priority Data

Dec. 19, 2016   (DE) .................. 10 2016 225 476

(51) Int. Cl.
*A61Q 5/10* (2006.01)
*A61K 8/55* (2006.01)
*A61Q 5/08* (2006.01)

(52) U.S. Cl.
CPC ............. *A61K 8/55* (2013.01); *A61Q 5/08* (2013.01); *A61Q 5/10* (2013.01); *A61K 2800/4324* (2013.01); *A61K 2800/884* (2013.01)

(58) Field of Classification Search
CPC ... A61Q 5/10; A61Q 5/08; A61K 8/55; A61K 8/24; A61K 2800/88; A61K 2800/4324
See application file for complete search history.

(56) References Cited

U.S. PATENT DOCUMENTS

| 2003/0147827 | A1 | 8/2003 | Decoster et al. |
| 2003/0157049 | A1 | 8/2003 | Gawtrey et al. |
| 2011/0168201 | A1 | 7/2011 | Bureiko et al. |
| 2014/0290686 | A1* | 10/2014 | Schweinsberg .......... A61Q 5/10 132/202 |

FOREIGN PATENT DOCUMENTS

| EP | 1771144 B1 | 7/2009 |
| WO | 2007141165 A1 | 12/2007 |

OTHER PUBLICATIONS

UKIPO Search Report in Application No. GB1721137.6 dated Aug. 16, 2018.

* cited by examiner

*Primary Examiner* — Eisa B Elhilo
(74) *Attorney, Agent, or Firm* — Lorenz & Kopf, LLP

(57) ABSTRACT

The subject matter of the present disclosure is a method for the oxidative lightening and/or dyeing of keratinous fibers, more particularly of hair, wherein
a) a dye and/or lightening agent is applied to the keratinous fiber, said dye or lightening agent being obtained by mixing a composition (A), which contains at least one alkalizing agent, with a composition (B), which contains, in a cosmetic carrier, at least one oxidant,
b) thereafter, within a period of one second to 24 hours after step a), a pre-treatment agent containing at least one salt of an isoalkylphosphoric acid ester, is applied to the keratinous fibers, more particularly the hair.

19 Claims, No Drawings

OXIDATIVE HAIR TREATMENT WITH POST-TREATMENT FOR IMPROVING FASTNESS TO WASHING

CROSS-REFERENCE TO RELATED APPLICATION

This application claims priority to German Patent Application No. 10 2016 225 476.6, filed Dec. 19, 2016, which is incorporated herein by reference in its entirety.

TECHNICAL FIELD

The present disclosure concerns a method for the oxidative lightening and/or dyeing of keratinous fibers, more particularly of hair, with improved fastness of the dyeing process, more particularly with improved fastness to washing, wherein the fastness to washing is improved more particularly on damaged fibers.

BACKGROUND

Although the oxidative dyeing, as well as the oxidative lightening, of hair, is considered as a "permanent" hair color change, the hair color achieved by employing the oxidation dyes is, of course, prone to reduction, be that through washing out as part of regular body hygiene, through sunlight or through bathing in water with a high proportion of salt or chlorine. Color on pre-damaged hair in particular usually has a low degree of fastness, more particularly fastness to washing. There is therefore a high demand for oxidative hair dyes and hair dyeing methods, by employing which an oxidative color with a high degree of fastness to washing, even and especially on pre-damaged hair, can be achieved.

In order to overcome the stated disadvantages, so-called post-treatment agents, which are declared "color seals" because they allegedly improve the fastness, more particularly the fastness to washing, of the color, are on the market. The effect of said agents, however, can be improved.

The present disclosure addressed the problem of providing a method for oxidative hair treatment with a post-treatment that improves the resistance of the hair color, said post-treatment overcoming the stated disadvantages without counteracting the success of the oxidative hair treatment achieved beforehand. More particularly, a method that does not impair the cosmetic properties of the hair was to be provided.

The use of aminized silicones in the hair product is known from the prior art. Said silicones are widely used in shampoos and more particularly in conditioners in order to develop nourishing effects. EP 1771144 B1, for example, discloses hair-conditioning agents having amino-functional silicones. The agents described therein are post-treatment agents.

European Patent EP 1312334 B1 (aminosilicone and thickener), as well as EP 1312335 B1 (aminosilicone and conditioner) disclose hair post-treatment agents.

For various reasons, the use of cosmetic products containing a silicone compound is not appreciated by all consumers. Said compounds tend to accumulate on the hair. The persistence thereof in the environment is the subject of discussion. Therefore, the present disclosure also addressed the problem of providing a method for oxidative hair treatment by employing a color-protecting post-treatment on the basis of non-silicones as an active ingredient.

BRIEF SUMMARY

Methods for the oxidative lightening and/or dyeing of keratinous fibers are provided herein. In an embodiment, in accordance with a method for the oxidative lightening and/or dyeing of keratinous fibers, a dye and/or lightening agent is applied to the keratinous fiber. The dye or lightening agent is obtained by mixing a composition (A), which includes at least one alkalizing agent, with a composition (B), which includes, in a cosmetic carrier, at least one oxidant. Within a period of from about one second to about 24 hours after applying the dye and/or lightening agent to the keratinous fiber, a post-treatment agent comprising at least one salt of an isoalkylphosphoric acid ester is applied to the keratinous fibers.

In another embodiment, in accordance with a method for the oxidative lightening and/or dyeing of keratinous fibers, a dye and/or lightening agent is applied to the keratinous fiber. The dye or lightening agent is obtained by mixing a composition (A), which includes at least one alkalizing agent, with a composition (B), which includes, in a cosmetic carrier, at least one oxidant. Within a period of from about one second to about 24 hours after applying the dye and/or lightening agent to the keratinous fiber, a post-treatment agent including at least one salt of an isoalkylphosphoric acid ester is applied to the keratinous fibers. The isoalkylphosphoric acid ester is obtained through the partial esterification of phosphoric acid with at least one branched non-ethoxylated C4-C12 alkanol and at least one branched ethoxylated C9-C17 alkanol selected from isononeth, isoundeceth, isotrideceth, isopentadeceth and isoheptadeceth with from about 5- about 10 ethoxy groups in the molecule.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has now emerged that post-treating keratinous fibers with special isoalkylphosphoric acid ester salts within a certain period of time after an oxidative hair treatment significantly improves the fastness to washing of the oxidative color, more particularly in the case of pre-damaged hair.

The subject matter of the present disclosure in a first embodiment is a method for the oxidative lightening and/or dyeing of keratinous fibers, more particularly of hair, wherein a) a dye and/or lightening agent is applied to the keratinous fiber, said dye or lightening agent being obtained by mixing a composition (A), which contains at least one alkalizing agent, with a composition (B), which contains, in a cosmetic carrier, at least one oxidant, b) thereafter, within a period of from about one second to about 24 hours after step a), a post-treatment agent containing at least one salt of an isoalkylphosphoric acid ester, is applied to the keratinous fibers, more particularly the hair.

Methods preferred as contemplated herein are exemplified in that the post-treatment agent used in step b) contains at least one salt of an isoalkylphosphoric acid ester, which is obtained through the partial esterification of phosphoric acid with at least one branched non-ethoxylated C4-C12 alkanol and at least one branched ethoxylated C9-C17 alkanol having an ethoxylation degree of from about 1 to about 20, preferably from about 4- about 15, more preferably from about 5- about 10.

Other methods preferred as contemplated herein are exemplified in that the at least one salt of an isoalkylphosphoric acid ester is selected from the potassium, sodium, lithium and ammonium salts, as well as the mixtures thereof, preferably the potassium and sodium salts, as well as the mixtures thereof.

Isoalkylphosphoric acid ester salts preferably used as contemplated herein, which are obtained through the partial esterification of phosphoric acid having at least one branched non-ethoxylated C4-C12-alkanol and having at least one branched ethoxylated C9-C17 alcohol having a degree of ethoxylation of from about 1 to about 20, preferably from about 4- about 15, more preferably from about 5- about 10 are exemplified in that the at least one branched, non-ethoxylated C4-C12-alkanol is selected from 2-ethylhexane-1-ol, 2-methylpropane-1-ol, 2-methylbutane-1-ol, 3-methylbutane-1-ol, 2,2-dimethylpropane-1-ol, 2-methylpentane-1-ol, 2-methylhexane-1-ol, 2-methylheptane-1-ol, 2-methyloctane-1-ol, 2-methylnonane-1-ol, 2-methyldecane-1-ol, 2-ethylpropane-1-ol, 2-ethylbutane-1-ol, 3-ethylbutane-1-ol, 2,2-diethylpropane-1-ol, 2-ethylpentane-1-ol, 2-ethylheptane-1-ol, 2-ethyloctane-1-ol, 2-ethylnonane-1-ol, 2-ethyldecane-1-ol, as well as the mixtures thereof, preferably selected from 2-ethylhexane-1-ol, 2-ethylbutane-1-ol, 2-ethyloctane-1-ol, 2-ethyldecane-1-ol, as well as the mixtures thereof, most preferably selected from 2-ethylhexane-1-ol.

Other isoalkylphosphoric acid ester salts preferably used as contemplated herein, which are obtained through the partial esterification of phosphoric acid having at least one branched non-ethoxylated C4-C12-alkanol and at least one branched ethoxylated C9-C17-alkanol having a degree of ethoxylation of from about 1 to about 20, preferably from about 4-about 15, more preferably from about 5- about 10, are exemplified in that the at least one branched ethoxylated C9-C17-alkanol having a degree of ethoxylation of from about 1 to about 20 is selected from isononeth, isodeceth, isoundeceth, isolaureth, isotrideceth, isomyreth, isopentadeceth, isoceteth and isoheptadeceth, each having from about 1 to about 20, preferably from about 4- about 15, more preferably from about 5- about 10, ethoxy groups in the molecule, as well as mixtures of said substances, wherein isononeth, isoundeceth, isotrideceth, isopentadeceth and isoheptadeceth each having from about 1 to about 20, preferably from about 4- about 15, more preferably from about 5- about 10, ethoxy groups in the molecule, as well as mixtures of said substances, are preferred.

Other isoalkylphosphoric acid ester salts preferably used as contemplated herein, which are obtained through the partial esterification of phosphoric acid having at least one branched non-ethoxylated C4-C12-alkanol and at least one branched ethoxylated C9-C17-alkanol having a degree of ethoxylation of from about 1 to about 20, preferably from about 4-about 15, more preferably from about 5- about 10, are exemplified in that the at least one salt of an isoalkylphosphoric acid ester is selected from the potassium salts of an isoalkylphosphoric acid ester, which is obtained through the partial esterification of phosphoric acid with 2-ethylhexyl alcohol and with isotrideceth-8.

An isoalkylphosphoric acid ester salt most preferably used as contemplated herein is a component having the INCI trade name of potassium ethylhexyl/isotrideceth-8 phosphate.

Other methods preferred as contemplated herein are exemplified in that the post-treatment agent used in step b, relative to the weight thereof, contains at least one salt of an isoalkylphosphoric acid ester in a total quantity of from about 0.001- about 5 wt. %, preferably from about 0.1- about 3 wt. %, more preferably from about 0.5- about 2 wt. %, and most preferably from about 1- about 1.5 wt. %, relative to the total weight of the post-treatment agent in each case. These quantity values apply, mutatis mutandis, for the embodiments of the isoalkylphosphoric acid ester salt preferred as contemplated herein, as described above.

Other methods preferred as contemplated herein are exemplified in that the post-treatment agent used in step b, relative to the weight thereof, contains potassium ethylhexyl/isotrideceth-8 phosphate in a total quantity of from about 0.001- about 5 wt. %, preferably from about 0.1- about 3 wt. %, more preferably from about 0.5- about 2 wt. %, and most preferably from about 1- about 1.5 wt. %, relative to the total weight of the post-treatment agent in each case.

Other methods preferred as contemplated herein are exemplified in that the post-treatment agent applied in method step b, relative to the weight thereof in each case, contains from about 70- about 97 wt. %, preferably from about 81- about 96 wt. %, most preferably from about 86- about 95 wt. % water.

Methods as contemplated herein are exemplified in that the post-treatment agent applied in step b, relative to the weight thereof in each case, contains from about 70- about 97 wt. %, preferably from about 81- about 96 wt. %, more preferably from about 86- about 95 wt. % water, and also at least one further hair-conditioning active ingredient, which is selected from linear C12-C30-alkanols, more particularly cetyl alcohol, stearyl alcohol, arachyl alcohol, behenyl alcohol and mixtures of said alcohols, from cosmetic oils, as well as from mixtures of said conditioning active ingredients.

Post-treatment agents preferably used as contemplated herein contain at least one linear C12-C30-alkanol, preferably selected from cetyl alcohol, stearyl alcohol, arachyl alcohol, behenyl alcohol and mixtures of said alcohols, in a total quantity of from about 0.01- about 5 wt. %, preferably from about 0.1- about 4 wt. %, more preferably from about 0.5- about 3 wt. %, relative to the weight of the post-treatment agent in each case.

Other post-treatment agents preferably used as contemplated herein contain at least one cosmetic oil in a total quantity of from about 0.01- about 5 wt. %, preferably from about 0.1- about 4 wt. %, more preferably from about 0.5- about 3 wt. %, relative to the weight of the post-treatment agent in each case.

It is preferable for the least one additional oil to be selected from natural and synthetic hydrocarbons, more preferably from mineral oil, paraffin oils, $C_{18}$-$C_{30}$-isoparaffins, particularly isoeicosane, polyisobutenes and polydecenes, $C_8$-$C_{16}$ isoparaffins, and 1,3-di (2-ethylhexyl)-cyclohexane; branched alkanols having a hydroxy group and from about 10 to about 50 carbon atoms; the benzoic esters of linear or branched $C_{8-22}$-alkanols; triglycerides of linear or branched, saturated or unsaturated, optionally hydroxylated $C_8$-30-fatty acids, in particular natural oils; the dicarboxylic acid esters of linear or branched $C_2$-$C_{10}$-alkanols; the esters of the linear or branched saturated or unsaturated fatty alcohols having from about 2 to about 30 carbon atoms, branched saturated or unsaturated fatty acids having from about 2 to about 30 carbon atoms, which can be hydroxylated; the addition products of from about 1 to about 5 propylene oxide units to mono- or polyhydric $C_8$-22-alkanols; the $C_8$-$C_{22}$-fatty alcohol esters of monohydric or polyhydric $C_2$-$C_7$-hydroxycarboxylic acids; the symmetrical, asymmetric or cyclic esters of carbonic acid with $C_{3-22}$-alkanols, $C_{3-22}$-alkane diols or $C_{3-22}$-alkane triols; the esters of dimeric unsaturated $C_{12}$-$C_{22}$-fatty acids (dimer fatty acids) with monovalent linear, branched or cyclic $C_2$-$C_{18}$-alkanols or with polyvalent linear or branched $C_2$-$C_6$-alkanols; silicone oils and mixtures of the aforementioned substances.

The post-treatment agents used as contemplated herein preferably have a viscosity (measured at 20° C.) in the range of from about 1000- about 50000 mPas, preferably from about 2000- about 10000 mPas. For this purpose, it can be preferable for the post-treatment agents used as contemplated herein to contain at least one thickening polymer, preferably in a total quantity of from about 0.2- about 5 wt. %, even more preferably from about 0.5- about 4 wt. %, and most preferably from about 0.8- about 2 wt. %, relative to the weight of the post-treatment agent in each case.

In another preferred embodiment, the post-treatment agent used as contemplated herein contains at last one naturally-occurring polymer thickening agent, which can be substituted with $C_1$-$C_6$-alkyl groups, $C_1$-$C_6$-hydroxyalkyl groups, carboxyalkyl groups, more particularly carboxymethyl groups and/or quaternary ammonium- or $C_1$-$C_6$-alkylammonium groups. Particularly preferred according to this embodiment are biosaccharide gums of microbial origin, more particularly xanthan gum, but also scleroglucangum, also gums from plant exsudates, such as rubber arabicum, ghatti rubber, karaya rubber, tragant rubber, carrageen rubber, agar-agar, guargums, locust bean flour, pectins, alginates, starch, starch fractions and derivatives, such as amylose, amylopectin, with 2-hydroxypropyl groups of etherified corn starch, as well as dextrines, also cellulose derivatives, such as methyl cellulose, carboxyalkyl celluloses and hydroxyalkyl celluloses, more particularly hydroxyethyl celluloses, and carboxyalkyl celluloses, more particularly carboxymethyl celluloses.

Post-treatment agents preferably used as contemplated herein contain xanthan gum, preferably from about 0.01 to about 3 wt. %, more preferably from about 0.1- about 1 wt. %, and most preferably from about 0.2- about 0.7 wt. % xanthan gum, relative to the weight of the post-treatment agent used as contemplated herein.

According to another preferred embodiment, the at least one thickening polymer is selected from anionic synthetic polymers, which preferably have carboxylate and/or sulfonate groups as anionic groups.

Examples of anionic monomers, of which the polymer anionic thickening agents can include, are acrylic acid, methacrylic acid, crotonic acid, itaconic acid, maleic anhydride and 2-acrylamido-2-methylpropane sulfonic acid. The acid groups can exist wholly or partially as sodium, potassium, ammonium, mono or triethanolammonium salt. Preferred monomers are maleic anhydride, as well as and more particularly 2-acrylamido-2-methylpropansulfonic acid and acrylic acids.

Preferred anionic homopolymers are non-cross-linked and cross-linked polyacrylic acids. Allylethers from pentaerythrite, sucrose and propylene can be preferred cross-linking agents. Such compounds are available in the trade under the trade name Carbopol®, for example. The homopolymer of 2-acrylamido-2-methylpropansulfonic acid is also preferred.

Within this first embodiment, the use of copolymers from at least one anionic monomer and at least one non-ionogenic monomer can also be preferred. With respect to anionic monomers, reference is made to the aforementioned substances. Preferred non-iogenic monomers are acryl amide, methacrylic amide, acrylic acid ester, methacrylic acid ester, itaconic acid mono- and -diester, vinyl pyrrolidinone, vinyl ether and vinyl ester.

Examples of preferred anionic copolymers are copolymers from acrylic acid, methacrylic acid or the $C_1$-$C_6$-alkyl esters thereof, as sold under the INCI declaration Acrylates Copolymer. A preferred commercial product is Aculyn® 33, for example. Also preferred, however, are copolymers from acrylic acid, methacrylic acid and the $C_1$-$C_6$-alkyl esters thereof, as well as the esters of an ethylenically unsaturated acid and an alkoxylated fatty alcohol. Suitable ethylenically unsaturated acids are, in particular, acrylic acid, methacrylic acid and itaconic acid; suitable alkoxylated fatty alcohols are, in particular, Steareth-20 or Ceteth-20. Such copolymers are sold under the trade name Aculyn® 22, as well as under the trade names Structure® 2001 and Structure® 3001.

Preferred anionic copolymers are also acrylic acid acrylamide copolymers, as well as, more particularly, polyacrylamide copolymers having sulfonic acid group-containing monomers. A particularly preferred anionic copolymer includes from about 70 to about 55 mol-% acryl amide and from about 30 to about 45 mol-% 2-acrylamido-2-methylpropane sulfonic acid, wherein the sulfonic acid group exists, either in whole or in part, as sodium, potassium, ammonium, mono or triethanol ammonium salt. This copolymer can also exist cross-linked, wherein polyolefinically unsaturated compounds, such as tetraallyloxythane, allylsucrose, allylpentaerythrite and methylen-bisacrylamide are preferably used as the cross-linking agents. This type of polymer is contained in the commercial products Sepigel® 305 and Simulgel® 600 from SEPPIC.

Polymers from maleic anhydride and methylvinyl ether, more particularly those with cross-linkage, are preferred thickening agents. A maleic acid-methylvinyl ether-copolymer cross-linked with 1,9-decadiene is commercially available under the trade name Stabileze® QM Preferably, the agent used as contemplated herein and in the method as contemplated herein additionally contains an anionic acrylic acid and/or methacrylic acid-polymerisate or methacrylic acid-copolymerisate. Preferred polymerisates of this type are:
  Polymerisates, e.g. from at least 10 wt. % acrylic acid-low alkyl ester, from about 25 to about 70 wt. % methacrylic acid and, where applicable, up to 40 wt. % of a further comonomer,
  mixed polymerisates from about 50 to about 75 wt. % ethyl acrylate, from about 25 to about 35 wt. % acrylic acid and from 0 to about 25 wt. % of other comonomers. Suitable dispersions of this type are commercially available, e.g. under the trade name Latekoll® D (BASF).
  Copolymerisates from about 50 to about 60 wt. % ethyl acrylate, from about 30 to about 40 wt. % methacrylic acid and from about 5 to about 15 wt. % acrylic acid, cross-linked with ethylenglycoldimethacrylate.

The anionic acrylic acid and/or methacrylic acid-polymerisates or copolymerisates are preferably used in the post-treatment agents as contemplated herein in a total quantity of from about 0.2- about 5 wt. %, more preferably from about 0.5- about 4 wt. %, and most preferably from about 0.8- about 2 wt. %, relative to the weight of the post-treatment agent in each case.

The post-treatment agent used as contemplated herein can be formulated as a water-based emulsion, preferably as an oil-in-water emulsion, but also as a spray, a cream, gel, lotion, paste, shampoo or conditioner.

The method as contemplated herein comprises an oxidative hair treatment and a subsequent application of a post-treatment agent to keratinous fibers within a period of from about one second to about 24 hours.

Methods preferred as contemplated herein are exemplified in that the period between method steps a and b of from about 2 seconds to about 20 minutes, is preferably from about 30 seconds to about 10 minutes, more preferably from about 1 to about 5 minutes.

Other methods preferred as contemplated herein are exemplified in that the post-treatment agent applied in method step b is left to act on the hair for a period of from about 2 seconds to about 120 minutes, preferably from about 5 seconds to about 10 minutes, before being rinsed out or before the hair is dried without rinsing out.

Other methods preferred as contemplated herein are exemplified in that the post-treatment agent applied in method step b is left to act on the hair for a period of from about 2 seconds to about 120 minutes, preferably from about 5 seconds to about 10 minutes, before being rinsed out or before one of the following method steps b)i):

Rinsing out the hair;
Drying the hair with a towel,
Drying the hair in the air;
Drying the hair with a hairdryer,
Drying the hair with a dryer hood,
Combination of the aforementioned method steps.

The drying process preferably occurs at a temperature of from about 20° C. to about 150° C.

Preferably, the hair is not rinsed out ahead of the drying process and/or the drying processes. A method preferred as contemplated herein is therefore exemplified in that the hair is not rinsed out after the application of the post-treatment agent in method step b and the drying process and/or the drying processes. However, it can also be preferred as contemplated herein for the hair to be rinsed out and then dried after step a), ahead of treatment step b.

A method preferred as contemplated herein is exemplified in that step a) comprises the application of a dye or lightening agent to the keratinous fibers, which is obtained by mixing a composition (A), which contains at least one alkalizing agent, with a composition (B), which contains in a cosmetic carrier at least one oxidant, wherein neither composition (A) nor composition (B) contains an aminized silicone compound.

It has unexpectedly emerged that a quantity of an aminized silicone compound in the oxidant, admitted through the alkalizing agent-containing composition (A) or the oxidation composition (B), can result in the fact that no improvement, or at least no improvement visible to the human eye, to the fastness to washing of the color by employing isoalkylphosphoric acid salts used as contemplated herein is achieved.

The composition (B) used in the method as contemplated herein contains, as a mandatory ingredient, at least one oxidant. Preferred oxidants are selected from peroxo compounds, preferably selected from hydrogen peroxide, solid addition compound of hydrogen peroxide on inorganic or organic compounds, such as sodium perborate, sodium percarbonate, magnesium percarbonate, sodium percarbamide, polyvinyl pyrrolidone $H_2O_2$ (n is a positive integer greater than 0), urea peroxide and melamine peroxide, also selected from diammonium peroxodisulfate (also referred to as ammonium persulfate), di-sodium peroxodisulfate (also referred to as sodium persulfate) and di-potassium peroxodisulfate (also referred to as potassium persulfate), as well as from mixtures of said oxidants. Oxidants most preferably used as contemplated herein are aqueous hydrogen peroxide solutions. The concentration of a hydrogen peroxide solution is determined on the one hand by legal requirements and, on the other hand, by the desired effect; from about 6 to about 12 wt. % solutions in water are generally used. Methods preferred as contemplated herein are exemplified in that the used composition (B)—relative to the weight thereof—contains from about 1 to about 24 wt. %, preferably from about 4- about 10 wt. %, more preferably from about 3- about 6 wt. % hydrogen peroxide (calculated as 100% $H_2O_2$).

The cosmetically tolerated carrier of composition (B) is preferably aqueous, alcoholic or aqueous-alcoholic. To the extent required by this present disclosure, aqueous-alcoholic carriers are aqueous compositions containing from about 3 to about 70 wt. % of a $C_1$-$C_4$ alcohol, relative to the total weight of composition (B), more particularly ethanol and/or isopropanol. Compositions (B) preferred as contemplated herein can additionally contain other organic solvents, such as methoxybutanol, ethyldiglycol, 1,2-propylenglycol, n-propanol, n-butanol, n-butylenglycol, glycerine, diethylenglycolmonoethylether, and diethylenglycolmono-n-butylether. All water-soluble organic solvents are preferred. To the extent required by the present disclosure, an aqueous carrier contains water in a total quantity of from about 35- about 97 wt. %, preferably from about 50- about 90 wt. %, more preferably from about 60- about 80 wt. %, relative to the total weight of composition (B) in each case.

As contemplated herein, composition (B) preferably has a weakly acidic pH value, preferably a pH value of from about 2 to about pH 6, more preferably from about pH 2.5 to about pH 4.5, and most preferably from about pH 3.0 to about pH 4.0. The pH values according to the present disclosure are pH values that were measured at a temperature of 22° C. The acidifying and alkalizing agents known to a person skilled in the art are commonly used to set the pH value. Acidifying agents as contemplated herein are flavoring acids, such as lactic acid, citric acid, acetic acid, malic acid or tartaric acid, as well as diluted mineral acids.

The composition (A) used in the method as contemplated herein and in the kit-of-parts as contemplated herein contains, as mandatory ingredient, at least one alkalizing agent. Oxidative dyeing processes on keratin fibers usually occur in an alkali environment. To protect the keratinous fibers and also the skin as much as possible, setting too high a pH value is however not desirable. Therefore, it is preferable for the pH value of the dye and/or lightening agent used in step b) is within the range from about 7 to about 11, more particularly within the range from about 8 to about 10.5. The pH values according to the present disclosure are pH values that were measured at a temperature of 22° C.

The alkalizing agents used to set the pH value preferred as contemplated herein can be selected from the group formed from ammonium hydroxide, basic amino acids, alkali hydroxides, alkanol amines, alkali metal metasilicates, alkaliphosphates and alkali hydrogen phosphates. Lithium, sodium and potassium, particularly sodium or potassium are preferred for use as alkali metal ions.

The basic amino acids that can be used as alkalizing agents are preferably selected from the group of L-arginine, D-arginine, D,L-arginine, L-lysine, D-lysine, D,L-lysine, L-arginine, D-arginine, D,L-arginine, are more preferably used as alkalizing agents as contemplated herein.

The alkali hydroxides that can be used as alkalizing agents are preferably selected from the group of sodium hydroxide and potassium hydroxide.

The alkanolamines usable as alkalization agents are preferably selected from primary amines with a $C_2$-$C_6$-alkyl base body having at least one hydroxyl group. More preferred alkanolamines are selected from the group comprising 2-aminoethan-1-ol (monoethanolamine), 3-aminopropan-1-ol, 4-amino-butan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. Most preferred alkanolamines as contemplated herein are selected from the group of 2-aminoethan-1-ol, 2-amino-2-methylpropan-1-ol and 2-amino-2-methyl-propan-1,3-diol.

For oxidative dyeing, immediately before the application on the fibers, more particularly the hair, a dye composition (A), containing at least one alkalizing agent and one or more oxidation dye precursors and, where applicable, one or more partially-oxidizing dyes, are usually mixed with a hydrous oxidant-containing composition (B) to produce the ready-to-use dye and then applied to the fibers, more particularly the hair.

For oxidative lightening, immediately before the application on the fibers, more particularly the hair, a lightening composition (A), containing at least one alkalizing agent and one or more partially-oxidizing dyes and, where applicable, one or more oxidation dye precursors, are usually mixed with an aqueous oxidant-containing composition (B) to produce the ready-to-use lightening agent and then applied to the fibers, more particularly the hair.

In most cases, the dye and/or lightening composition (A) and the oxidant-containing composition (M2) are matched with one another such that, at a mixing ratio of 1 to 1, relative to the parts by weight, the dye or lightening agent has an initial concentration of hydrogen peroxide of from about 0.5- about 12 wt. %, preferably from about 2- about 10 wt. %, more preferably from about 3- about 6 wt. % of hydrogen peroxide (calculated as 100% $H_2O_2$), in each case relative to the weight of the application mixture. However, it is equally possible for the dye and/or lightening composition (A) and the oxidant-containing composition (B) to be matched to one another such that the concentrations required in the ready-to-use dye and/or lightening agent is achieved through mixture ratios other than 1:1, for example through a weight-based mixture ratio of 1:2 or 1:3 or even 2:3. Methods preferred as contemplated herein are exemplified in that the ready-to-use dye and/or lightening agent used in method step b) contains an initial quantity of hydrogen peroxide of from about 0.5- about 12 wt. %, preferably from about 2- about 10 wt. %, more preferably from about 3- about 6 wt. % hydrogen peroxide (calculated as 100% $H_2O_2$) relative to the weight of the dye and/or lightening agent.

Weight-based mixture ratios preferred as contemplated herein (M1):(M2) are within the range from about 1:0.8 to about 1:2.5, more preferably within the range of from about 1:1 to about 1:2.

Methods and kits-of-parts as contemplated herein are exemplified in that the ready-to-use dye and/or lightening agent used in method step b) contains at least one cosmetic oil in a total quantity of from about 5- about 50 wt. %, preferably from about 8- about 40 wt. %, more preferably from about 12- about 30 wt. %, and most preferably from about 15- about 25 wt. %, relative to the weight of the dye and/or lightening agent in each case.

To achieve a color that requires a strong lightening of very dark hair, the use of hydrogen peroxide or the addition products thereof on organic and/or inorganic compounds is often inadequate. In such cases, a combination of hydrogen peroxide and peroxide sulfate salts (persulfate salts) is normally used. Preferred persulfate salts are ammonium peroxidisulfate, potassium oxide sulfate, sodium peroxide sulfate, as well as the mixtures thereof.

The at least one persulfate salt is preferred in a total quantity of from about 0.1 to about 25 wt. %, more preferably in a total quantity of from about 1 to about 15 wt. %, relative to the weight of the ready-to-use dye.

Methods and kits-of-parts preferred as contemplated herein are exemplified in that composition (B) used as contemplated herein contains at least one cosmetic oil in a total quantity of from about 12- about 70 wt. %, preferably from about 14- about 60 wt. %, more preferably from about 15- about 52 wt. % and most preferably from about 17- about 35 wt. %, relative to the weight of composition (B) in each case.

Other methods and kits-of-parts preferred as contemplated herein are exemplified in that composition (B) used as contemplated herein contains at least one tenside.

In selecting tensides suitable as contemplated herein, it is most preferable to use a mixture of tensides in order to optimally set the stability of the oxidant composition (B) used as contemplated herein.

Methods and kits-of-parts preferred as contemplated herein are exemplified in that the tenside contained composition (B) is selected from non-ionic tensides and anionic tensides, as well as the mixtures thereof.

The oxidant composition (B) preferably used as contemplated herein contains a total of from about 0.1 to about 5 wt. %, preferably from about 0.5 to about 3 wt. % and most preferably from about 1- about 2 wt. %, relative to the total weight of oxidant composition (B), of a mixture of non-ionic and ionic tensides.

Other methods as contemplated herein are exemplified in that the composition (B) used as contemplated herein contains at least one linear saturated alkanol having from about 12- about 30 carbon atoms.

Preferred linear saturated alkanols having from about 12- about 30 carbon atoms, more particularly having from about 16- about 22 carbon atoms, are selected from cetyl alcohol, stearyl alcohol, arachidyl alcohol, behenyl alcohol and lanolin alcohol, as well as mixtures of said alcohols. Alkanol mixtures particularly preferred as contemplated herein are those that can be obtained from the technical hydration of plant and animal fatty acids. Preferably, the total quantity of the at least one linear saturated alkanol having from about 12- about 30 carbon atoms in the oxidant composition (B) from about 0.1- about 10 wt. %, preferably from about 0.5- about 7 wt. % and more preferably from about 3- about 5 wt. %, relative to the total weight of the oxidant composition (B) in each case.

Other methods and kits-of-parts preferred as contemplated herein are exemplified in that composition (B):
contains from about 1 to about 24 wt. %, preferably from about 4- about 10 wt. %, more preferably from about 3- about 6 wt. % hydrogen peroxide (calculated as 100% $H_2O_2$), also at least one cosmetic oil in a total quantity of from about 12- about 70 wt. %, preferably from about 14- about 60 wt. %, more preferably from about 15- about 52 wt. % and most preferably from about 17- about 35 wt. %, also at least one tenside in a total quantity of from about 0.1 to about 5 wt. %, preferably from about 0.5 to about 3 wt. % and more preferably from about 1 to about 2 wt. %, as well as at least one linear saturated alkanol having from about 12- about 30 carbon atoms in a total quantity of from about 0.1 to about 10 wt. %, preferably from about 0.5 to about 7 wt.

% and more preferably from about 3 to about 5 wt. %, wherein all wt. % values refer to the weight of composition (B).

As a mandatory ingredient for the dyeing method and an optional ingredient for the lightening method, composition (A) used in the method as contemplated herein contains at least one oxidation dye precursor of the developer type and at least one oxidation dye precursor of the coupler type.

On the basis of their reaction behavior, oxidative dye precursors can be divided into two categories, so-called developer components and coupler components.

During the oxidative dyeing process, coupler components do not achieve any significant coloration by themselves. They always require the presence of developer components. Developer components can combine together to form the actual dye.

The developer and coupler components are normally used in a free form. In the case of substances with amino groups, however, use of the salt form thereof, more particularly in the form of hydrochlorides and hydrobromides or sulfates, may be preferred.

It has unexpectedly emerged that the method as contemplated herein is able to achieve, using at least one oxidation dye precursor of the developer type and at least one oxidation dye precursor of the coupler type, hair colors having particularly high fastness to washing.

Particularly preferred developer components are selected from at least one compound from the group formed from p-phenylendiamine, p-toluylendiamine, 2-(2-hydroxyethyl)-p-phenylendiamine, 2-(1,2-dihydroxyethyl)-p-phenylendiamine, N,N-bis-(2-hydroxyethyl)-p-phenylendiamine, 2-methoxymethyl-p-phenylendiamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropane-2-ol, bis-(2-hydroxy-5-aminophenyl)methane, 1,3-bis-(2,5-diaminophenoxy)propane-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl) pyrazol, 2,4,5,6-tetraaminopyrimidine, 4-hydroxy-2,5,6-triaminopyrimidine, 2-hydroxy-4,5,6-triaminopyrimidine, the physiologically tolerated salts of said compounds, as well as the mixtures of said developer components and developer component salts.

More particularly preferred developer components are selected from 4,5-diamino-1-(2-hydroxyethyl)pyrazole, p-toluylendiamine, 2-(2-hydroxyethyl)-p-phenylendiamine, 2-methoxymethyl-p-phenylendiamine, N-(4-amino-3-methylphenyl)-N-[3-(1H-imidazol-1-yl)propyl]amine and mixtures thereof, as well as the physiologically tolerated salts thereof. Most preferred is 4,5-diamino-1-(2-hydroxyethyl) pyrazole, as well as the physiologically-tolerable salts thereof.

The developer components are preferably used in a total quantity of from about 0.01- about 20 wt. %, more preferably from about 0.2- about 10 wt. %, and most preferably from about 0.6- about 5 wt. %, relative to the weight of composition (A) in each case.

The developer components are preferably used in a total quantity of from about 0.005- about 10 wt. %, more preferably from about 0.1- about 5 wt. %, and most preferably from about 0.3- about 2.5 wt. %, relative to the weight of the ready-to-use dye in each case.

To the extent required by this application, the expression "ready-to-use dye and/or lightening agent" means the mixture from composition (A) and composition (B). A particularly suitable cosmetic carrier for composition (A) is a cream basis.

As contemplated herein, coupler components permit at least one substitution of a chemical radical of the coupler through the oxidized form of the developer components. At the same time, a covalent bond forms between coupler and developer components. Couplers are preferably cyclic compounds which carry at least two groups on the cyclus, selected from (i) possibly substituted amino groups and/or and/or (ii) hydroxyl groups. If the cyclical compound is a six-membered ring (preferably aromatic), said groups are preferably located in the ortho position or the meta position.

Methods preferred as contemplated herein are exemplified in that at least one oxidation dye precursor of the coupler type is selected from one of the following classes:

3-aminophenol (m-aminophenol) and/or the derivatives thereof, 3-aminoanilin (m-diaminobenzol) and/or the derivatives thereof, 2-aminoanilin (1,2-diaminobenzol; o-diaminobenzol) and/or the derivatives thereof, 2-aminophenol (o-aminophenol) and/or the derivatives thereof, naphthaline derivatives having at least one hydroxy group, di- and/or trihydroxybenzol and/or the derivatives thereof, pyridine derivatives, pyrimidine derivatives, monohydroxyindol derivatives and/or monoaminoindol-derivatives, monohydroxyindolin derivatives and/or monoaminoindolin derivatives, pyrazolone derivatives, such as 1-phenyl-3-methylpyrazol-5-on, morpholine derivatives, such as 6-hydroxybenzomorpholine or 6-aminobenzomorpholine, quinoxaline derivatives, such as 6-methyl-1,2,3,4-tetrahydroquinoxaline, Mixtures of two or multiple compounds from one or multiple of said classes are likewise preferred according to this embodiment.

Coupler components particularly preferred as contemplated herein are selected from 3-aminophenol, 5-amino-2-methylphenol, 3-amino-2-chlor-6-methylphenol, 2-hydroxy-4-aminophenoxy ethanol, 5-amino-4-chlor-2-methylphenol, 5-(2-hydroxyethyl)amino-2-methylphenol, 2,4-dichlor-3-aminophenol, 2-aminophenol, 3-phenylendiamine, 2-(2,4-diaminophenoxy)ethanol, 1,3-bis(2,4-diaminophenoxy)propane, 1-methoxy-2-amino-4-(2'-hydroxyethylamino)benzol (=2-amino-4-hydroxyethylaminoanisol), 1,3-bis (2,4-diaminophenyl) propane, 2,6-bis(2'-hydroxyethylamino)-1-methylbenzol, 2-({3-[(2-hydroxyethyl)amino]-4-methoxy-5-methylphenyl}amino)ethanol, 2-({3-[(2-hydroxyethyl) amino]-2-methoxy-5-methylphenyl}amino)ethanol, 2-({3-[(2-hydroxyethyl)amino]-4,5-dimethylphenyl}amino) ethanol, 2-[3-morpholine-4-ylphenyl)amino]ethanol, 3-amino-4-(2-methoxyethoxy)-5-methylphenylamin, 1-amino-3-bis-(2-hydroxyethyl)aminobenzol, resorcin, 2-methylresorcin, 4-chlorresorcin, 1,2,4-trihydroxybenzol, 2-amino-3-hydroxypyridine, 3-amino-2-methylamino-6-methoxypyridin, 2,6-dihydroxy-3,4-dimethylpyridin, 3,5-diamino-2,6-dimethoxypyridin, 1-phenyl-3-methylpyrazol-5-on, 1-naphthol, 1,5-dihydroxynaphthalin, 2,7-dihydroxynaphthalin, 1,7-dihydroxynaphthalin, 1,8-dihydroxynaphthalin, 4-hydroxyindol, 6-hydroxyindol, 7-hydroxyindol, 4-hydroxyindolin, 6-hydroxyindolin, 7-hydroxyindolin or mixtures of said compounds or the physiologically tolerated salts of said compounds.

Most preferred are 3-aminophenol, resorcin, 2-methylresorcin, 5-amino-2-methylphenol, 2-(2,4-diaminophenoxy) ethanol, 1,3-bis(2,4-diaminophenoxy)propane, 1-methoxy-2-amino-4-(2'-hydroxyethylamino)benzol, 2-amino-3-hydroxypyridine and 1-naphthol, as well as the physiologically tolerated salts and mixtures of said components.

The at least one coupler component is preferably used in a total quantity of from about 0.01- about 20 wt. %, more preferably from about 0.2- about 10 wt. %, and most preferably from about 0.6- about 5 wt. %, relative to the weight of composition (A) in each case.

The at least one coupler component is preferably used in a total quantity of from about 0.005- about 10 wt. %, more preferably from about 0.1- about 5 wt. %, and most preferably from about 0.3- about 2.5 wt. %, relative to the weight of the ready-to-use oxidation dye in each case.

According to the present disclosure, the following combinations of oxidation dye precursors of the developer type and of the coupler type are particularly preferred, wherein the amine compounds and the nitrogen heterocycles can also exist in the form of the physiologically tolerated salts thereof:

p-toluylendiamine/resorcin;
p-toluylendiamine/2-methylresorcin;
p-toluylendiamine/5-amino-2-methylphenol;
p-toluylendiamine/3-aminophenol;
p-toluylendiamine/2-(2,4-diaminophenoxy)ethanol;
p-toluylendiamine/1,3-bis(2,4-diaminophenoxy)propane;
p-toluylendiamine/1-methoxy-2-amino-4-(2-hydroxyethylamino)benzol;
p-toluylendiamine/2-amino-3-hydroxypyridine;
p-toluylendiamine/1-naphthol;
2-(2-hydroxyethyl)-p-phenylendiamine/resorcin;
2-(2-hydroxyethyl)-p-phenylendiamine/2-methylresorcin;
2-(2-hydroxyethyl)-p-phenylendiamine/5-amino-2-methylphenol;
2-(2-hydroxyethyl)-p-phenylendiamine/3-aminophenol;
2-(2-hydroxyethyl)-p-phenylendiamine/2-(2,4-diaminophenoxy)ethanol;
2-(2-hydroxyethyl)-p-phenylendiamine/1,3-bis(2,4-diaminophenoxy)propane;
2-(2-hydroxyethyl)-p-phenylendiamine/1-methoxy-2-amino-4-(2-hydroxyethylamino)benzol;
2-(2-hydroxyethyl)-p-phenylendiamine/2-amino-3-hydroxypyridin;
2-(2-hydroxyethyl)-p-phenylendiamine/1-naphthol;
2-methoxymethyl-p-phenylendiamine/resorcin;
2-methoxymethyl-p-phenylendiamine/2-methylresorcin;
2-methoxymethyl-p-phenylendiamine/5-amino-2-methylphenol;
2-methoxymethyl-p-phenylendiamine/3-aminophenol;
2-methoxymethyl-p-phenylendiamine/2-(2,4-diaminophenoxy)ethanol;
2-methoxymethyl-p-phenylendiamine/1,3-bis(2,4-diaminophenoxy)propane;
2-methoxymethyl-p-phenylendiamine/1-methoxy-2-amino-4-(2-hydroxyethylamino)benzol;
2-methoxymethyl-p-phenylendiamine/2-amino-3-hydroxypyridin;
2-methoxymethyl-p-phenylendiamine/1-naphthol;
N-(4-amino-3-methylphenyl)-N-[3-(1H-imidazol-1-yl)propyl]amin/resorcin;
N-(4-amino-3-methylphenyl)-N-[3-(1H-imidazol-1-yl)propyl]amin/2-methylresorcin;
N-(4-amino-3-methylphenyl)-N-[3-(1H-imidazol-1-yl)propyl]amin 5-amino-2-methylphenol;
N-(4-amino-3-methylphenyl)-N-[3-(1H-imidazol-1-yl)propyl]amin/3-aminophenol;
N-(4-amino-3-methylphenyl)-N-[3-(1H-imidazol-1-yl)propyl]amin 2-(2,4-diaminophenoxy)ethanol;
N-(4-amino-3-methylphenyl)-N-[3-(1H-imidazol-1-yl)propyl]amin 1,3-Bis(2,4-diaminophenoxy)propane;
N-(4-amino-3-methylphenyl)-N-[3-(1H-imidazol-1-yl)propyl]amin/1-methoxy-2-amino-4-(2-hydroxyethylamino)benzol;
N-(4-amino-3-methylphenyl)-N-[3-(1H-imidazol-1-yl)propyl]amin 2-amino-3-hydroxypyridin;
N-(4-amino-3-methylphenyl)-N-[3-(1H-imidazol-1-yl)propyl]amin/1-naphthol;
4,5-diamino-1-(2-hydroxyethyl)pyrazol/resorcin;
4,5-diamino-1-(2-hydroxyethyl)pyrazol/2-methylresorcin;
4,5-diamino-1-(2-hydroxyethyl)pyrazol/5-amino-2-methylphenol;
4,5-diamino-1-(2-hydroxyethyl)pyrazol/3-aminophenol;
4,5-diamino-1-(2-hydroxyethyl)pyrazol/2-(2,4-diaminophenoxy)ethanol;
4,5-diamino-1-(2-hydroxyethyl)pyrazol/1,3-bis(2,4-diaminophenoxy)propane;
4,5-diamino-1-(2-hydroxyethyl)pyrazol/1-methoxy-2-amino-4-(2-hydroxyethylamino)benzol;
4,5-diamino-1-(2-hydroxyethyl)pyrazol/2-amino-3-hydroxypyridin;
4,5-diamino-1-(2-hydroxyethyl)pyrazol/1-naphthol.

As contemplated herein, particularly preferable with respect to the improvement to the fastness to washing are the combinations of 4,5-diamino-1-(2-hydroxyethyl)pyrazol/3-aminophenol/toluene-2,5-diaminsulfate/4-amino-2-hydroxytoluol, p-toluylendiamine/4-amino-2-hydroxytoluol/4-amino-3-methylphenol and p-toluylendiamin/4-amino-2-hydroxytoluol/4-amino-3-methylphenol/2,7-dihydroxynaphthalin.

To achieve a balanced and subtle tint formation, it is preferable as contemplated herein for further chromophoric components are contained in the dye, which is used in the method as contemplated herein.

In another embodiment, the agents used in step b) of this variant of the method as contemplated herein can additionally contain at least one partially-oxidizing dye. Partially-oxidizing dyes are dyes that coat the substrate itself and do not require an oxidative process to create the color. Partially-oxidizing dyes are usually nitro-phenylendiamines, nitroaminophenols, azo dyes, anthraquinones or indophenols.

Another method preferred as contemplated herein is exemplified in that the dye and/or lightening agent applied in step b) is rinsed off the fibers after a period of from about 5-about 60 minutes, preferably from about 15- about 50 minutes, more preferably from about 30- about 45 minutes.

The dye used in step b of the method as contemplated herein is produced from a two-component agent, wherein one component, namely the composition (A) contains at least one alkalizing agent and, where applicable, the oxidation dye precursors and/or partially-oxidizing agents, and the other components, namely the composition (B), contains the oxidant or oxidants. The ready-to-use dye and/or lightening agent for step b is then produced by mixing the two components immediately before application step b. Optionally, at least one further component, for example a blonding powder, an additional alkalizing agent or a nourishing component, e.g. an oil, can be added to the mixture of (A) and (B). A separation into multi component systems is preferred in particular wherever the ingredients are expected to be or suspected of being incompatible.

A further subject matter of the present disclosure is therefore a kit-of-parts, comprising
(i) a first Container (C1) with a post-treatment agent, containing at least one salt of an isoalkylphosphoric acid ester,
and also
(ii) a second Container (C2) with a composition (A), containing at least one alkalizing agent
(iii) and also a third Container (C3) with a composition (B), containing in a cosmetic carrier at least one oxidant.

The statements above regarding the preferred embodiments of the method as contemplated herein also apply, mutatis mutandis, to the kit-of-parts as contemplated herein.

The following examples are intended to explain the subject matter of the present disclosure without having any limiting effect.

Typical Embodiments and Fastness to Washing Tests

TABLE 1

Composition (A-1): Dye cream (quantity values in wt. %)

| Cetylalcohol | 3.60 |
| Stearylalcohol | 2.00 |
| Paraffin oil | 2.10 |
| Ceteareth-30 | 1.20 |
| Steareth-100 | 0.60 |
| Glycerylstearate (1:1 mixture from glyceryl monostearate and glyceryl distearate) | 0.60 |
| 1,2-propanediol | 6.00 |
| Acrylamidopropyltrimonium chloride/Acrylate Copolymer* | 0.80 |
| Ammonium hydroxide | 3.20 |
| Toluene-2,5-diaminsulphate | 0.16 |
| 1-hydroxyethyl 4,5-diaminopyrazolsulfate | 1.04 |
| 3-aminophenol | 0.44 |
| 4-amino-2-hydroxytoluol | 0.12 |
| 2(4-methyl-2-nitrophenyl)aminoethanol | 0.20 |
| pyrogenic silica | 0.25 |
| Monoethanolamine | 2.00 |
| Sodium sulfate | 0.30 |
| Ascorbic acid | 0.10 |
| Tetrasodium EDTA | 0.20 |
| Ammonium sulfate | 0.70 |
| Perfume | 0.80 |
| Water | 73.59 |

*zwitterionic polymer according to DE3929973A1, production example 1

TABLE 2

Oxidant-containing developers (B-1) for the dye cream from Table 1

| Ingredient | Test sample (wt. %) |
|---|---|
| Sodium benzoate | 0.04 |
| Dipicolinic acid (2,6-dicarboxypyridine) | 0.10 |
| Di-sodium pyrophosphate | 0.10 |
| Potassium hydroxide | 0.10 |
| 1,2-propanediol | 0.50 |
| Etidronic acid | 0.15 |
| Paraffin oil | 2.00 |
| Cetearyl alcohol | 3.40 |
| Ceteareth-20 | 1.00 |
| Hydrogen peroxide | 6.00 |
| Water | ad 100.00 |

The aforementioned composition (A)-1 was mixed, in a ratio of 1:1, with the composition (B)-1=oxidant composition (B) shown in Table 2 to form a ready-to-use dye. The ready-to-use dye was then immediately applied to severely damaged (twice-permed, twice-blonded) hair strands (Kerling medium blond), more specifically 5 g dye per gram of hair, for the fastness to washing test.

TABLE 3

Composition (A-2): Dye cream (quantity values in wt. %)

| Cetearyl alcohol | 6.60 |
| Coco alcohol* | 2.40 |
| Ceteareth-20 | 0.60 |
| Ceteareth-12 | 0.60 |
| Coco glucoside | 0.60 |
| Glyceryl monooleate | 0.60 |
| Sodium laureth-6-carboxylate | 2.00 |
| Natriummyreth-2-sulfate | 2.00 |
| Acrylamidopropyltrimonium chloride/Acrylate Copolymer* | 0.80 |
| Sodium hydroxide | 0.07 |
| Ammonium hydroxide | 3.30 |
| Ammonium sulfate | 0.90 |
| Toluene-2,5-diaminsulfate | 0.19 |
| 2-amino-6-chlor-4-nitrophenol | 0.11 |
| 4-amino-2-hydroxytoluol | 0.13 |
| 2,7-dihydroxynaphthalin | 0.17 |
| 4-amino-3-methylphenol | 0.36 |
| Soluble glass | 0.50 |
| Sodium sulfate | 0.40 |
| Ascorbic acid | 0.10 |
| Etidronic acid | 0.10 |
| Sodium hydroxide | 0.35 |
| Perfume | 0.80 |
| Water | 76.32 |

TABLE 4

Oxidant-containing developers (B-2) for the dye cream from Table 3

| Ingredient | Test sample (wt. %) |
|---|---|
| Sodium hydroxide | 0.40 |
| Dipicolinic acid (2,6-dicarboxypyridin) | 0.10 |
| Di-sodium pyrophosphate | 0.03 |
| Etidronic acid | 0.15 |
| Mixture of cross-linked (meth)acrylic acid/acrylic acid-C1-C6-alkyl ester copolymers (ex Aculyn 33A) | 4.20 (active) |
| Sodium laureth(2)sulphate | 0.50 |
| Hydrogen peroxide | 6.00 |
| Water | ad 100.00 |

* Aculyn 33A: hydrous dispersion of Acrylates Copolymer (mixture of cross-linked (meth)acrylic acid/acrylic acid-C1-C6-alkyl ester copolymers); 28 wt. % polymer content (active substance)

The aforementioned composition (A)-2 was mixed, in a ratio of 1:1, with the composition (B)-2=oxidant composition (B) shown in Table 4 to form a ready-to-use dye. The ready-to-use dye was then immediately applied to severely damaged (once-blonded) hair strands (Kerling medium blond), more specifically 5 g dye per gram of hair, for the fastness to washing test.

TABLE 5

Composition (A-3): Dye cream (quantity values in wt. %)

| Ingredient | |
|---|---|
| Sodium cetearyl sulfate | 0.50 |
| Sodium laureth(2)sulphate | 1.00 |
| Potassium hydroxide | 0.08 |
| Oleic acid | 0.30 |
| Cetearyl alcohol | 9.60 |
| Ceteareth-20 | 2.40 |
| 2-octyldodecanol | 1.50 |
| Glycerol | 0.20 |
| Glycerylstearate (1:1 mixture | 2.80 |

TABLE 5-continued

Composition (A-3): Dye cream (quantity values in wt. %)

| Ingredient | |
|---|---|
| from glyceryl monostearate and glyceryl distearate) | |
| Potassium stearate | 0.20 |
| Sodium sulfate | 0.30 |
| Ammonium hydroxide | 4.70 |
| Tetranatrium EDTA | 0.20 |
| Ascorbic acid | 0.05 |
| 1-hydroxyethyl 4,5-iaminopyrazolsulfate | 1.50 |
| 4-amino-3-methylphenol | 0.20 |
| 4-amino-2-hydroxytoluol | 0.30 |
| 3-aminophenol | 0.60 |
| Carbomer | 0.12 |
| Water | 68.70 |

The aforementioned composition (A-3) was mixed, in a ratio of 1:1, with the composition (B-1) shown in Table 2 to form a ready-to-use dye. The ready-to-use dye was then immediately applied to severely damaged (twice-permed, twice-blonded) hair strands (Kerling medium blond), more specifically 5 g dye per gram of hair, for the fastness to washing test.

TABLE 6

Post-treatment agent b used as contemplated herein

| Ingredient | Test sample (wt. %) |
|---|---|
| Potassium ethylhexyl/isotrideceth-8 phosphate | 1.00 |
| Sodium cetearyl sulfate | 0.36 |
| Cetearyl alcohol | 3.50 |
| PEG-40 Castor Oil | 0.70 |
| Hydrogen peroxide | 6.00 |
| Water | ad 100.00 |

The dye (mixture (A-1) plus (B-1) and/or mixture (A-2) plus (B-2) remain on the strands for 30 minutes each. The strands are then rinsed with warm tap water at a temperature of 32° C. and a flow rate of 0.5 liters per minute for a period of 2 minutes.

Half the dyed and rinsed strands were then immediately dipped in an aqueous emulsion of an isoalkyl phosphoric acid ester salt according to the formula shown in Table 5 for a period of 10 minutes. The strands were then removed from the dipping bath, rinsed with water and dried.

The other half of the dyed and rinsed strands remained without any post-treatment as contemplated herein.
After being dried, all dyed test strands were washed in an aqueous solution with 10 wt. % sodium laureth(2)sulfate and a pH value of 3.5 for 60 minutes in the ultrasonic bath at 45° C. This procedure simulates 24 hair washes. The strands were then rinsed and dried.

To assess the color loss caused by shampooing, the color difference ΔE measured on the respective strands was determined.

The color difference, also referred to as dE or ΔE, can readily be determined by colorimetry by employing a colorimeter, via which the colors in the L*,a*,b* color space were measured, a colorimeter from Datacolor, Type Spectraflash 450, for example.

The L*,a*,b* color space means the CIELAB color space. The L-value denotes the lightness of the color (black-white axis); the higher the value for L, the lighter the color. The a-value denotes the red-green axis of the system; the higher this value, the more the color is shifted into the red. The b-value denotes the yellow-blue axis of the system; the higher this value, the more the color is shifted into the yellow.

The color shift ΔE, i.e. the color difference between two (hair) colors, for which a L*,a*,b* value combination was determined in each case, is calculated according to the following formula:

$$\Delta E = (\Delta L^2 + \Delta a^2 + \Delta b^2)^{0.5}$$

The higher the value for ΔE, the more pronounced the color difference, i.e. the higher the amount of color washed out and the lower the fastness to washing of the dye.

Table 7:

Fastness to washing after simulation of 24 washing cycles; value for L a b color difference ΔE $$\Delta E = E_{without\ post\text{-}treatment} - E_{with\ post\text{-}treatment\ as\ contemplated\ herein}$$

| Dye | Substrate | E-value without post-treatment | E-value with post treatment | ΔE |
|---|---|---|---|---|
| (A-1) plus (B-1) | severely damaged | 22.6 | 17.5 | 5.1 |
| (A-2) plus (B-2) | undamaged | 10.7 | 8.6 | 2.1 |
| (A-2) plus (B-2) | slightly damaged | 17.1 | 11.5 | 5.5 |
| (A-3) plus (B-1) | severely damaged | 11.9 | 10.4 | 1.5 |

As the data displayed in Table 7 shows, the post-treatment agent used as contemplated herein was able to improve the fastness to washing of the dye, more particularly in the case of damaged hair.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Method for the oxidative lightening and/or dyeing of keratinous fibers, wherein
    a) a dye and/or lightening agent is applied to the keratinous fiber, said dye or lightening agent being obtained by mixing a composition (A), which comprises at least one alkalizing agent, with a composition (B), which comprises, in a cosmetic carrier, at least one oxidant,
    b) thereafter, within a period of from about one second to about 24 hours after step a), a post-treatment agent comprising at least one salt of an isoalkylphosphoric acid ester, is applied to the keratinous fibers.

2. Method according to claim 1, wherein the post-treatment agent used in step b) comprises at least one salt of an isoalkylphosphoric acid ester, which is obtained through the partial esterification of phosphoric acid with at least one branched non-ethoxylated C4-C12 alkanol and at least one branched ethoxylated C9-C17 alkanol having an ethoxylation degree of from about 1 to about 20.

3. Method according to claim 1, wherein the at least one salt of an isoalkylphosphoric acid ester is selected from the potassium, sodium, lithium, ammonium salts, or mixtures thereof.

4. Method according to claim 2, wherein the at least one branched, non-ethoxylated C4-C12-alkanol is selected from 2-ethylhexane-1-ol, 2-methylpropane-1-ol, 2-methylbutane-1-ol, 3-methylbutane-1-ol, 2,2-dimethylpropane-1-ol, 2-methylpentane-1-ol, 2-methylhexane-1-ol, 2-methylheptane-1-ol, 2-methyloctane-1-ol, 2-methylnonane-1-ol, 2-methyldecane-1-ol, 2-ethylpropane-1-ol, 2-ethylbutane-1-ol, 3-ethylbutane-1-ol, 2,2-diethylpropane-1-ol, 2-ethylpentane-1-ol, 2-ethylheptane-1-ol, 2-ethyloctane-1-ol, 2-ethylnonane-1-ol, 2-ethyldecane-1-ol, or mixtures thereof.

5. Method according to claim 2, wherein the at least one branched ethoxylated C9-C17 alkanol having an ethoxylated degree of from about 1 to about 20 is selected from isononeth, isodeceth, isoundeceth, isolaureth, isotrideceth, isomyreth, isopentadeceth, isoceteth and isoheptadeceth, or mixtures thereof.

6. Method according to claim 1, wherein the at least one salt of an isoalkylphosphoric acid ester is selected from the potassium salts of an isoalkylphosphoric acid ester, which is obtained through the partial esterification of phosphoric acid with 2-ethylhexylalcohol and with isotrideceth-8.

7. Method according to claim 1, wherein the post-treatment agent used in step b comprises the at least one salt of an isoalkylphosphoric acid ester in a total quantity of from about 0.001- about 5 wt. %, relative to the total weight of the post-treatment agent.

8. Method according to claim 1, wherein the post-treatment agent applied in step b comprises from about 70- about 97 wt. % water, and, optionally, at least one further hair-conditioning active ingredient, which is selected from linear C12-C30-alkanols, cosmetic oils, or mixtures of said conditioning active ingredients, wherein the wt. % is relative to the total weight of the post-treatment agent.

9. Method according to claim 1, wherein the composition (A) also comprises at least one oxidation dye precursor of the developer type and at least one oxidation dye precursor of the coupler type.

10. Method according to claim 1, wherein neither the composition (A) nor the composition (B) contain an aminized silicone compound.

11. Method according to claim 1, wherein the post-treatment agent used in step b) comprises at least one salt of an isoalkylphosphoric acid ester, which is obtained through the partial esterification of phosphoric acid with at least one branched non-ethoxylated C4-C12 alkanol and at least one branched ethoxylated C9-C17 alkanol having an ethoxylation degree of from about 5- about 10.

12. Method according to claim 1, wherein the at least one salt of an isoalkylphosphoric acid ester is selected from the potassium salts, sodium salts, or mixtures thereof.

13. Method according to claim 1, wherein the at least one branched, non-ethoxylated C4-C12-alkanol is 2-ethylhexane-1-ol.

14. Method according to claim 5, wherein the at least one branched ethoxylated C9-C17 alkanol having an ethoxylated degree of from about 1 to about 20 is selected from isononeth, isoundeceth, isotrideceth, isopentadeceth, and isoheptadeceth or mixtures thereof.

15. Method according to claim 1, wherein at least one salt of an isoalkylphosphoric acid ester is selected from the potassium salts of an isoalkylphosphoric acid ester, which is obtained through the partial esterification of phosphoric acid with 2-ethylhexylalcohol and with isotrideceth-8.

16. Method according to claim 1, wherein the post-treatment agent used in step b comprises at least one salt of an isoalkylphosphoric acid ester in a total quantity of from about 1- about 1.5 wt. %, relative to the total weight of the post-treatment agent.

17. Method according to claim 1, wherein the post-treatment agent applied in step b comprises from about 86- about 95 wt. % water, relative to the total weight of the post-treatment agent.

18. Method according to claim 1, wherein the post-treatment agent applied in step b comprises at least one further hair-conditioning active ingredient, which is selected from linear C12-C30-alkanols, cosmetic oils, or mixtures of said conditioning active ingredients.

19. Method for the oxidative lightening and/or dyeing of keratinous fibers, wherein
  a) a dye and/or lightening agent is applied to the keratinous fiber, said dye or lightening agent being obtained by mixing a composition (A), which comprises at least one alkalizing agent, with a composition (B), which comprises, in a cosmetic carrier, at least one oxidant,
  b) thereafter, within a period of from about one second to about 24 hours after step a), a post-treatment agent comprising at least one salt of an isoalkylphosphoric acid ester, which is obtained through the partial esterification of phosphoric acid with at least one branched non-ethoxylated C4-C12 alkanol and at least one branched ethoxylated C9-C17 alkanol selected from isononeth, isoundeceth, isotrideceth, isopentadeceth and isoheptadeceth, is applied to the keratinous fibers.

* * * * *